US006288245B1

(12) United States Patent
Bertola

(10) Patent No.: US 6,288,245 B1
(45) Date of Patent: Sep. 11, 2001

(54) PROCESS FOR THE PRODUCTION OF TETRAHYDROFURAN AND GAMMABUTYROLACTONE

(75) Inventor: Aldo Bertola, Milan (IT)

(73) Assignee: Pantochim S.A., Feluy (BE)

( * ) Notice: Subject to any disclaimer, the term of this patent is extended or adjusted under 35 U.S.C. 154(b) by 0 days.

(21) Appl. No.: 09/367,044

(22) PCT Filed: Jan. 5, 1999

(86) PCT No.: PCT/EP99/00013

§ 371 Date: Aug. 6, 1999

§ 102(e) Date: Aug. 6, 1999

(87) PCT Pub. No.: WO99/35136

PCT Pub. Date: Jul. 15, 1999

(30) Foreign Application Priority Data

Jan. 8, 1998 (BE) .................................................. 9800013

(51) Int. Cl.⁷ ...................... C07D 307/08; C07D 307/20
(52) U.S. Cl. ........................... 549/326; 549/508; 549/509
(58) Field of Search ..................................... 549/326, 508, 549/509

(56) References Cited

U.S. PATENT DOCUMENTS 4,105,674    8/1978    De Thomas et al. .

FOREIGN PATENT DOCUMENTS

| 8607358 | 12/1986 | (WO) . |
| 0322140 | 6/1989 | (WO) . |
| 9743234 | 11/1997 | (WO) . |

OTHER PUBLICATIONS

Miya et al., Prepr. Div. Pet. Chem., Am. Chem. Soc. 18(1) pp. 187–192, 1973.*

* cited by examiner

Primary Examiner—Taofiq A. Solola
(74) Attorney, Agent, or Firm—Stevens, Davis, Miller & Mosher, LLP

(57) ABSTRACT

A two-stage process for producing tetrahydrofuran and gammabutyrolactone in varying proportions from maleic, succinic anhydride or fumaric acid esters, by vapor phase hydrogenation. The first stage occurs on a copper-based catalyst to produce a mixture of tetrahydrofuran, gammabutyrolactone and butanediol. The second stage occurs on an acidic silica rich silica-alumina type catalyst to convert butanediol to tetrahydrofuran.

16 Claims, 1 Drawing Sheet

PROCESS FOR THE PRODUCTION OF TETRAHYDROFURAN AND GAMMABUTYROLACTONE

Figure 1:
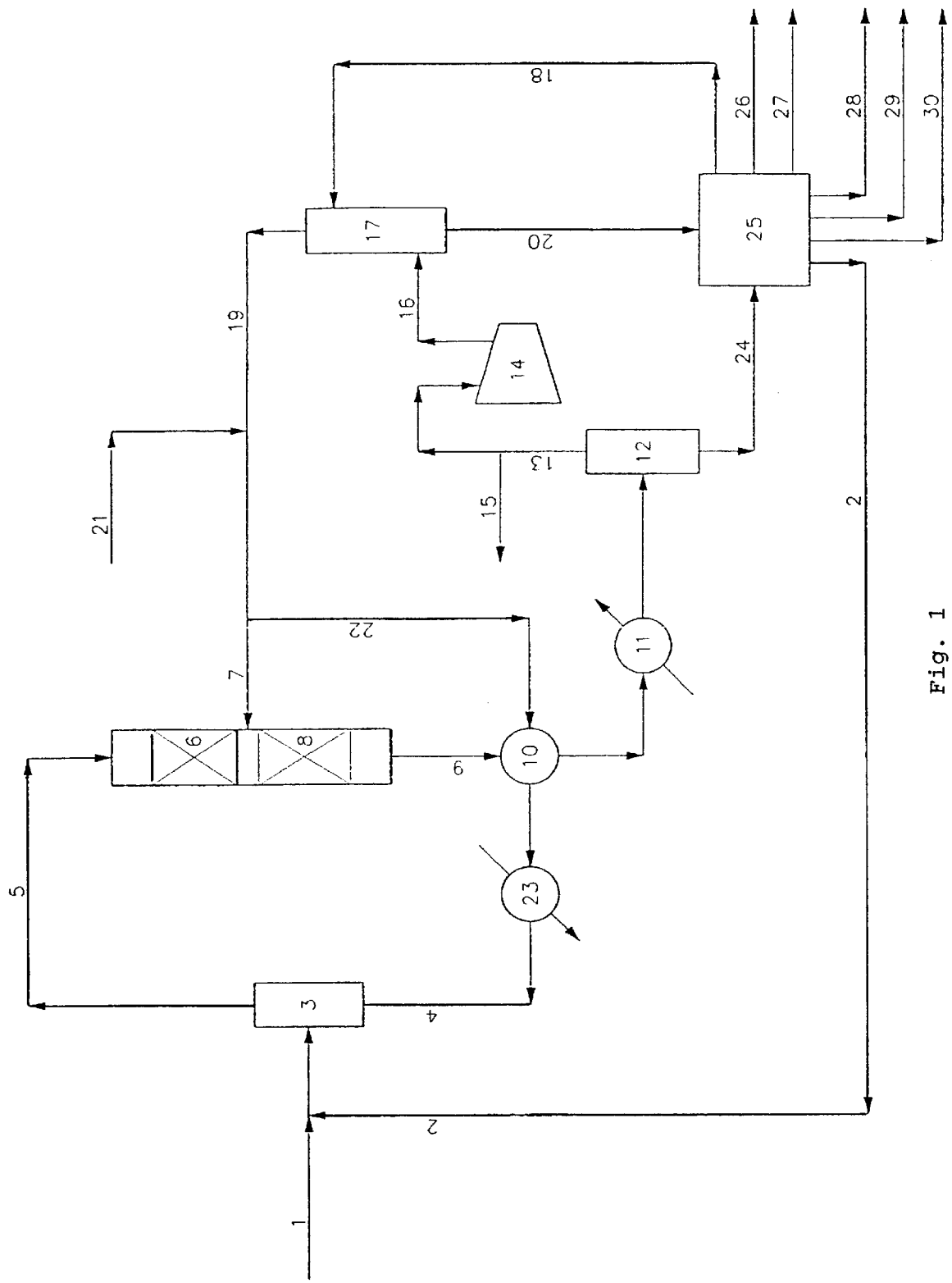

This application is a 371 of PCT/EP99/00013 filed Jan. 5, 1999.

DESCRIPTION

The present invention relates to a process for the production of tetrahydrofuran and gammabutyrolactone, particularly to a process starting from maleic, succinic anhydride or fumaric acid esters, by vapour phase hydrogenation in two subsequent stages, the former on a copper based catalyst, the latter on an acid silica rich silica-alumina type catalyst.

Tetrahydrofuran is a solvent used extensively in organic chemistry, and on the industrial scale it is in high demand for the production of natural and synthetic resins Gammabutyrolactone is on the other hand among the other things a useful solvent for acrylate and styrene polymers.

It is known from the prior art that there exist several methodologies that can be employed for the production of Tetrahydrofuran (THF) and Gammabutyrolactone (GBL).

THF is produced starting from butanediol (BDO), by a process involving dehydration GBL too is produced starting from BDO by a process involving dehydrogenation. The production of THF and GBL starting from BDO is particularly costly because of the relatively high costs inherent with BDO, whose production involves rather complex processes.

According to a method which is widely utilised by industry, BDO is produced allowing acetylene to react with formaldehyde, with concomitant formation of butynediol which subsequently undergoes hydrogenation to form BDO.

Mitsubishi Chemical Industries of Japan has developed a process for the production of BDO starting from Butadiene.

The synthetic strategy comprises butadiene acetoxylation to 1,4-diacetoxy-2-butene, which is subsequently hydrogenated and hydrolized to BDO.

General Electric Corporation patented a process for the production of BDO starting from propylene. The synthetic pathway in this case includes conversion of propylene to allyl acetate, subsequently converted to 4-acetoxybutanol which forms BDO after hydrolysis.

Special attention has been devoted to the development of processes in which butane is utilised as starting material, through the formation of a maleic anhydride intermediate.

Several processes have been proposed for the production of THF, GBL or BDO starting from maleic anhydride, its esters or similar esters like succinic and/or fumaric acid esters.

U.S. Pat. Nos. 4,584,419 and 4,751,334 assigned to Davy McKee Ltd. describe processes for the production of BDO by hydrogenation of carboxylic acid esters that contain 4 Carbon atoms (typically ethyl maleate).

In International Patent WO 86/07358, this too assigned to Davy McKee Ltd, an account is given for a process where GBL is produced starting from maleic anhydride or the homologous dicarboxylic acid esters, by hydrogenation carried out in the vapour phase and in two subsequent stages on a chromite type catalyst.

In EP No. 322 140 in the name of Standard Oil Company, a process for the production of THF and GBL is given, starting from maleic or succinic anhydride, by a single stage hydrogenation on a catalyst made up of a copper, zinc and aluminium based mixture.

The aim of the present invention is to propose a process for the production of THF and GBL in varying proportions, starting from maleic anhydride and/or succinic acid and/or fumaric acid esters, all of these obtained allowing the acids or anhydrides thereof to react with an alcohol containing from 1 to 4 Carbon atoms.

According to the present invention the process is based on the production of tetrahydrofuran and gammabutyrolactone, by vapour phase selective hydrogenation of maleic anhydride, succinic anhydride and/or fumaric acid esters, characterised by the fact that the hydrogenation takes place in two subsequent stages, of which the former takes place on a copper based catalyst, and the latter on an acidic silica-alumina type catalyst that is rich in silica.

These and other features will be more readily apparent from the following description of a preferred not limiting embodiment of the invention with reference to the accompanying drawing in which a scheme of the production process is shown.

In the process object of the present invention the ester, after being completely vapourised by a hydrogen rich stream, is fed to a reactor characterised by two distinct reaction stages. The first stage contains a copper based heterogeneous hydrogenation catalyst, with a preference given to copper-zinc oxide or stabilised copper chromite type catalysts.

The subsequent reaction stage contains an acidic silica enriched silica-alumina type heterogeneous catalyst.

To allow the reaction to take place in the vapour phase, the reaction mixture must be very rich in hydrogen.

The hydrogen to ester molar ratio ranges between 100 and 600:1, preferably between 200 and 400:1.

Pressure and temperature as well as catalyst contact times in each reaction stage may be optimised depending on the choice of the GBL:THF product ratio. Such ratio may be varied within a wide range, that is GBL:THF ratios that go from 70:30 to 40:60.

The average operating pressure ranges between 3 and 40 bars, preferably from 15 to 25 bars In both reaction stages, temperatures range between 180 and 280° C., and typically between 200 and 250° C.

Overall Liquid Hourly Space Velocity ranges between 0.1 and 0.5 $hr^{-1}$.

The space velocity with which the gaseous mixture goes on the catalyst (gaseous space velocity on the catalyst) in the second reaction stage results to be 1.5 to 10 times higher than that on the catalyst of the first reaction stage.

A cooling between the first and second reaction stage can be carried out in a heat exchanger or more simply by mixing the cold hydrogen mixture to the effluent in the first reaction stage.

In FIG. 1, a typical process scheme is shown in the enclosed drawing.

Operating conditions refer to a starting material consisting of dimethylsuccinate (DMS).

The process is essentially feasible even in case the starting material consists of carboxylic acid esters with 4 Carbon atoms.

The ester feedstock (Line 1) is fed to vapouriser 3 together with a recycle stream (line 2) that contains BDO and unconverted DMS, from product fractionation unit 25.

The recycle stream usually includes GBL which yields an azeotropic mixture with DMS.

In vapouriser 3, the feed (Line 5) and the recycle (Line 2), come in contact with a hot hydrogen stream (Line 4), and they vapourise.

In the gas stream from the vapouriser (Line 5) the Hydrogen:shot molar ratio is 200, temperature is 210° C., pressure is 15 Technical Atmosphere (ATE).

Such stream feeds the first stage of reaction 6 which contains a copper-zinc oxide type catalyst.

Temperature at the outlet of the first stage is taken down from approx 225° C. to approx. 200° C. by injection of a cold hydrogen stream (Line 7).

In the second stage of reaction 8, gases flow on an acidic silica-alumina type catalyst rich in silica.

A catalyst employed in the process is an acidic mordenite or zeolite, with an apparent bulk density (ABD) of 0.65 and surface area equalling 450 $m^2 gr^{-1}$.

At the outlet of the second reaction stage, the overall conversion is as high as 97%, with the following product yields:

| | | |
|---|---|---|
| GBL | | 53% |
| THF | | 34% |
| BDO | | 7% |
| Byproducts | | 3% |

Liquid Hourly Space Velocity is as high as 0.2 $hr^{-1}$.

The effluent from the second stage of reaction (line 9) cools down in exchanger 10 giving heat to the recycle hydrogen rich stream, and in exchanger 11, to eventually feed separator 12, where the condensed organic phase separates from the hydrogen rich gaseous phase.

The gaseous phase at the outlet of separator 12 (Line 13) is compressed by compressor 14, to be recycled to the reaction system.

A fraction of the recycle gas is purged (line 15) to hinder deposition of inert materials.

Compressed gas (line 16) feeds column 17, where it comes to contact with a GBL rich stream (line 18) that comes from product fractionation unit 25.

Recycle gases are washed with a GBL rich stream, and this allows the vapour phase present in the gases to be effectively removed.

As known, water is a by-product of THF synthesis. An efficient removal of water, as that obtained washing the recycle gas with a GBL enriched liquid stream, is important to avoid deterioration of the copper based catalyst.

After the wash, the GBL enriched stream (line 20) gets back to by-product fractionation unit 25, where the water which had been previously absorbed is removed.

Dried gases (line 19), together with the hydrogen feed (line 21) partly (line 7) mix with the effluents from Stage 1 of reactor 6 and partly (line 22) preheat in exchanger 23, to eventually feed vapouriser 3.

The liquid phase at the outlet of separator 12 feeds (line 24) a product fractionation unit 25, where THF (line 26), methanol (line 27), GBL (line 28), a fraction containing BDO and DMS which is recycled to the reaction (line 2), heavy organic byproducts (line 29), water and light organic byproducts (line 30) are separated.

The entire process allows direct and simple production of GBL and THF, with a high degree of flexibility, avoiding all the complications which are proper of other production processes, where GEL and THF are produced employing BDO as starting material.

What is claimed is:

1. A process for the production of tetrahydrofuran (THF) and gammabutyrolactone (GBL), comprising vapour phase selective hydrogenation of maleic anhydride, succinic anhydride and/or fumaric acid esters, wherein the hydrogenation takes place in first and second sequential stages, wherein the hydrogenation in the first stage takes place on a copper based catalyst, and the hydrogenation in the second stage takes place on an acidic silica-alumina catalyst that is rich in silica and;

discharging a stream comprising tetrahydrofuran and gammabutyrolactone from the second stage.

2. A process according to claim 1, wherein the ester alkyl component contains from 1 to 4 carbon atoms.

3. A process according to claim 1 wherein the hydrogenation operating pressure ranges between 3 and 40 bars, and operating temperature ranges between 180 and 280° C.

4. A process according to claim 1, wherein the hydrogenation operating pressure ranges between 15 and 25 bars.

5. A process according to claim 1 wherein the hydrogen to ester ratio in the reactor ranges between 100/1 and 600/1.

6. A process according to claim 5, wherein the hydrogen to ester ratio in the reactor ranges between 200/1 and 400/1.

7. A process according to claim 1 wherein the ratio of produced gammabutyrolactone (GBL) to tetrahydrofuran (THF) ranges between 70/30 and 40/60.

8. A process according to claim 1, wherein in the first hydrogenation stage the catalyst is copper-zinc oxide or of the copper chromite type and it is coupled in the second stage with a catalyst rich in silica.

9. A process according to claim 1 wherein a catalyst employed in the second stage is an acidic mordenite or zeolite.

10. A process according to claim 8, wherein the copper chromite is stabilised.

11. A process according to claim 5, wherein in the second stage the catalyst has a specific surface area ranging between 50 and 800 $m^2 g^{-1}$.

12. A process according to claim 9 wherein the apparent bulk density (ABD) of the catalyst is 0.65 and its surface area equals 450 $m^2 gr^{-1}$.

13. A process according to claim 1 wherein the catalyst in the second stage contains at least 80% silica.

14. A process according to claim 1, wherein the vapour phase mixture containing hydrogen and ester flows on the catalysts with a liquid hourly space velocity that ranges between 0.1 and 0.5 $hr^{-1}$.

15. A process according to claim 1, wherein the vapour phase travels on the reaction second stage catalyst with a space velocity which is 1.5 to 10 times higher than that on the catalyst of the reaction first stage.

16. A process according to claim 1, wherein the hydrogen rich recycle stream is washed downstream from the reaction with a butyrolactone rich stream, to remove the steam present in the recycle gas.

* * * * *